US008828368B2

(12) United States Patent
Fack et al.

(10) Patent No.: US 8,828,368 B2
(45) Date of Patent: Sep. 9, 2014

(54) COSMETIC COMPOSITION COMPRISING A PARTICULAR ZINC SALT AND A STARCH

(75) Inventors: Géraldine Fack, Levallois (FR); Boris Lalleman, Paris (FR); Julie Brun, Asnieres sur Seine (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/995,984

(22) PCT Filed: Dec. 20, 2011

(86) PCT No.: PCT/EP2011/073345
§ 371 (c)(1),
(2), (4) Date: Sep. 16, 2013

(87) PCT Pub. No.: WO2012/084904
PCT Pub. Date: Jun. 28, 2012

(65) Prior Publication Data
US 2013/0344018 A1    Dec. 26, 2013

Related U.S. Application Data

(60) Provisional application No. 61/431,633, filed on Jan. 11, 2011.

(30) Foreign Application Priority Data

Dec. 21, 2010    (FR) .................................... 10 60904

(51) Int. Cl.
| | | |
|---|---|---|
| A61K 8/00 | (2006.01) | |
| A61K 8/73 | (2006.01) | |
| A61K 8/23 | (2006.01) | |
| A61K 8/58 | (2006.01) | |
| A61K 8/20 | (2006.01) | |
| A61K 8/27 | (2006.01) | |
| A61Q 5/00 | (2006.01) | |
| A61K 8/368 | (2006.01) | |
| A61K 8/365 | (2006.01) | |
| A61Q 5/12 | (2006.01) | |
| A61K 8/46 | (2006.01) | |

(52) U.S. Cl.
CPC . *A61K 8/58* (2013.01); *A61K 8/732* (2013.01); *A61K 8/23* (2013.01); *A61K 8/20* (2013.01); *A61K 8/27* (2013.01); *A61Q 5/004* (2013.01); *A61K 8/368* (2013.01); *A61K 8/365* (2013.01); *A61Q 5/12* (2013.01); *A61K 8/463* (2013.01)
USPC ........................................ 424/70.1; 424/70.4

(58) Field of Classification Search
USPC ................................................ 424/70.1, 70.4
See application file for complete search history.

(56) References Cited

U.S. PATENT DOCUMENTS

| | | |
|---|---|---|
| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby |
| 2,388,614 A | 11/1945 | Kirby et al. |
| 2,454,547 A | 11/1948 | Bock et al. |
| 2,961,347 A | 11/1960 | Floyd |
| 3,206,462 A | 9/1965 | McCarty |
| 3,227,615 A | 1/1966 | Korden |
| 3,472,840 A | 10/1969 | Stone et al. |
| 3,632,559 A | 1/1972 | Matter et al. |
| 3,874,870 A | 4/1975 | Green et al. |
| 3,910,862 A | 10/1975 | Barabas et al. |
| 3,912,808 A | 10/1975 | Sokol |
| 3,917,817 A | 11/1975 | Vanlerberghe et al. |
| 3,929,990 A | 12/1975 | Green et al. |
| 3,966,904 A | 6/1976 | Green et al. |
| 3,986,825 A | 10/1976 | Sokol |
| 4,001,432 A | 1/1977 | Green et al. |
| 4,005,193 A | 1/1977 | Green et al. |
| 4,013,787 A | 3/1977 | Varlerberghe et al. |
| 4,017,460 A | 4/1977 | Tessler |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,008 A | 5/1977 | Sokol |
| 4,027,020 A | 5/1977 | Green et al. |

(Continued)

FOREIGN PATENT DOCUMENTS

| | | |
|---|---|---|
| EP | 0 080 976 A1 | 6/1983 |
| EP | 0 095 238 A2 | 11/1983 |
| EP | 0 122 324 A1 | 10/1984 |
| EP | 0 239 346 A2 | 9/1987 |
| EP | 0 337 354 A1 | 10/1989 |
| EP | 0 530 974 A1 | 3/1993 |
| EP | 1 051 967 A2 | 11/2000 |
| EP | 1 568 351 A1 | 8/2005 |
| EP | 1 776 983 A1 | 4/2007 |
| EP | 1 923 042 A1 | 5/2008 |
| FR | 1 492 597 | 8/1967 |
| FR | 1 583 363 | 10/1969 |
| FR | 2 077 143 | 10/1971 |
| FR | 2 080 759 | 11/1971 |
| FR | 2 162 025 | 7/1973 |
| FR | 2 190 406 | 2/1974 |
| FR | 2 252 840 | 5/1975 |

(Continued)

OTHER PUBLICATIONS

International Search Report for PCT/EP2011/073345.

(Continued)

*Primary Examiner* — Elisa Elhilo
(74) *Attorney, Agent, or Firm* — The Marbury Law Group, PLLC

(57) ABSTRACT

The present invention relates to a cosmetic composition comprising, in a cosmetically acceptable medium, at least one non-nitrogenous zinc salt and at least one starch, in a weight ratio of the amount of starch to the amount of zinc element ranging from 0.01 to 20. Another subject of the invention relates to a process for treating keratin fibers, using such a composition, and to the use of such a composition, preferably in the form of a leave-on care product, for conditioning keratin fibers and for protecting their artificial color from fading.

20 Claims, No Drawings

(56) References Cited

U.S. PATENT DOCUMENTS

| | | | |
|---|---|---|---|
| 4,075,136 A | 2/1978 | Schaper | |
| 4,137,180 A | 1/1979 | Naik et al. | |
| 4,157,388 A | 6/1979 | Christiansen | |
| 4,165,367 A | 8/1979 | Chakrabarti | |
| 4,172,887 A | 10/1979 | Vanlerberghe et al. | |
| 4,185,087 A | 1/1980 | Morlino | |
| 4,189,468 A | 2/1980 | Vanlerberghe et al. | |
| 4,197,865 A | 4/1980 | Jacquet et al. | |
| 4,217,914 A | 8/1980 | Jacquet et al. | |
| 4,223,009 A | 9/1980 | Chakrabarti | |
| 4,240,450 A | 12/1980 | Grollier et al. | |
| 4,277,581 A | 7/1981 | Vanlerberghe et al. | |
| 4,348,202 A | 9/1982 | Grollier et al. | |
| 4,349,532 A | 9/1982 | Vanlerberghe et al. | |
| 4,381,919 A | 5/1983 | Jacquet et al. | |
| 4,390,689 A | 6/1983 | Jacquet et al. | |
| 4,422,853 A | 12/1983 | Jacquet et al. | |
| 4,445,521 A | 5/1984 | Grollier et al. | |
| 4,579,732 A | 4/1986 | Grollier et al. | |
| 4,608,250 A | 8/1986 | Jacquet et al. | |
| 4,652,445 A | 3/1987 | Ort | |
| 4,702,906 A | 10/1987 | Jacquet et al. | |
| 4,719,099 A | 1/1988 | Grollier et al. | |
| 4,719,282 A | 1/1988 | Nadolsky et al. | |
| 4,777,040 A | 10/1988 | Grollier et al. | |
| 4,839,166 A | 6/1989 | Grollier et al. | |
| 4,874,554 A | 10/1989 | Lange et al. | |
| 4,948,579 A | 8/1990 | Jacquet et al. | |
| 4,970,066 A | 11/1990 | Grollier et al. | |
| 4,996,059 A | 2/1991 | Grollier et al. | |
| 5,009,880 A | 4/1991 | Grollier et al. | |
| 5,089,252 A | 2/1992 | Grollier et al. | |
| 5,196,189 A | 3/1993 | Jacquet et al. | |
| 5,374,334 A | 12/1994 | Sommese et al. | |
| 5,455,340 A | 10/1995 | Bernard et al. | |
| 5,681,554 A | 10/1997 | Cannell et al. | |
| 5,958,392 A | 9/1999 | Grollier et al. | |
| 6,426,383 B1 | 7/2002 | Fong et al. | |
| 6,894,110 B2 | 5/2005 | Fong et al. | |
| 7,713,310 B2 | 5/2010 | Lalleman | |
| 8,449,871 B2 | 5/2013 | Mougin et al. | |
| 2002/0198317 A1 | 12/2002 | Fong et al. | |
| 2003/0129210 A1 | 7/2003 | Chowdhary | |
| 2004/0110650 A1 | 6/2004 | Siddiqui et al. | |
| 2006/0039882 A1 | 2/2006 | Demitz et al. | |
| 2006/0067907 A1 | 3/2006 | Mougin et al. | |
| 2007/0009472 A1* | 1/2007 | Niebauer et al. | 424/70.28 |
| 2007/0283977 A1 | 12/2007 | Mougin et al. | |
| 2008/0134449 A1 | 6/2008 | Lalleman | |
| 2008/0229521 A1 | 9/2008 | Lalleman | |
| 2009/0176675 A1* | 7/2009 | Peffly et al. | 510/121 |
| 2009/0176676 A1 | 7/2009 | Peffly et al. | |
| 2010/0147319 A1 | 6/2010 | Lalleman | |
| 2010/0147320 A1 | 6/2010 | Lalleman | |

FOREIGN PATENT DOCUMENTS

| | | |
|---|---|---|
| FR | 2 270 846 | 12/1975 |
| FR | 2 280 361 | 2/1976 |
| FR | 2 316 271 | 1/1977 |
| FR | 2 320 330 | 3/1977 |
| FR | 2 336 434 | 7/1977 |
| FR | 2 368 508 | 5/1978 |
| FR | 2 383 660 | 10/1978 |
| FR | 2 393 573 | 1/1979 |
| FR | 2 413 907 | 8/1979 |
| FR | 2 470 596 | 6/1981 |
| FR | 2 519 863 | 7/1983 |
| FR | 2 598 611 A1 | 11/1987 |
| FR | 2 875 503 A1 | 3/2006 |
| FR | 2 898 603 A1 | 9/2007 |
| FR | 2 944 967 A1 | 11/2010 |
| GB | 1 331 819 | 9/1973 |
| GB | 1 546 809 | 5/1979 |
| WO | 02/49587 A1 | 6/2002 |
| WO | 03/084487 A1 | 10/2003 |
| WO | 2007/005577 A2 | 1/2007 |

OTHER PUBLICATIONS

International Search Report for PCT/EP2011/073296.
Co-pending U.S. Appl. No. 13/996,067; National Stage of International Application No. PCT/EP2011/073296; Boris Lalleman et al., "Composition Comprising a Non-Nitrogenous Zinc Salt and a Particular Cationic Surfactant," filed Jun. 20, 2013.

* cited by examiner

COSMETIC COMPOSITION COMPRISING A PARTICULAR ZINC SALT AND A STARCH

This is a national stage application of PCT/EP2011/073345, filed internationally on Dec. 20, 2011, which claims priority to U.S. Provisional Application No. 61/431,633, filed on Jan. 11, 2011; as well as French Application FR 1060904, filed on Dec. 21, 2010.

The present invention relates to a cosmetic composition comprising at least one particular zinc salt and at least one starch in particular weight ratio, and also to the use of such a composition, preferably in the form of a rinse-off or leave-on care product, for conditioning keratin fibres and protecting their artificial colour from fading.

It is known practice to dye the hair with dye compositions containing oxidation dye precursors, which are generally known as oxidation bases. These oxidation bases are colourless or weakly coloured compounds, which, when combined with oxidizing products, give rise to coloured compounds via a process of oxidative condensation. It is also known that the shades obtained with these oxidation bases can be varied by combining them with couplers or coloration modifiers. The variety of molecules used as oxidation bases and couplers allows a wide range of colours to be obtained.

It is also known practice to the hair by direct dyeing. The process conventionally used in direct dyeing consists in applying to the hair direct dyes, which are coloured and colouring molecules that have affinity for the hair, in leaving them to stand on the hair and then in rinsing the fibres.

The colorations resulting therefrom are particularly chromatic colorations but are, however, only temporary or semi-permanent since the nature of the interactions that bind the direct dyes to the keratin fibre and their desorption from the surface and/or the core of the fibre are responsible for their weak dyeing power and their poor fastness with respect to washing.

The artificial colour of the hair afforded by a direct dyeing or oxidation dyeing treatment gradually attenuates on repeated washing and exposure to light, leading over time to fading of the coloration of the hair.

Besides the impairment of the artificial colours, the hair is also damaged by repeated washing, various dyeing-bleaching treatments and also mechanical treatments such as combing and brushing. In general, care products such as hair conditioners, leave-on masks or leave-on care products are used to make the hair beautiful while affording a good level of treatment. The use of fatty esters in such care products is known.

However, the formulation of zinc salts in such care products poses numerous difficulties: inter alia, the formulation of zinc salts, especially in the presence of cationic silicones, leads to compositions that are usually unstable over time and are thus unmarketable.

Thus, there is a need to find cosmetic compositions, especially in the form of a leave-on care product, which can both protect the artificial colour of the hair against the various attacking factors responsible for the fading of the colours (repeated washing, sunlight) and afford the hair a good level of care, and which are stable over time.

The Applicant has discovered, surprisingly, that by formulating cosmetic compositions comprising at least one particular zinc salt and at least one starch in a particular ratio, the drawbacks mentioned above can be overcome, by obtaining compositions that are stable over time, which show satisfactory protection of the artificial colour of the hair against fading of the coloration of the hair, giving the hair good cosmetic properties, and which can be used as rinse-off or leave-on care products.

In particular, the composition according to the invention is stable over time. In particular, it shows satisfactory stability on storage both at room temperature (25° C.) and at higher temperature (for example 37 or 45° C.). This means that the composition of the invention has a texture that changes little or not at all over time and in particular which does not show any syneresis effect over time.

In addition, the composition according to the invention affords more supple hair, which has a smoother feel and is better coated.

Thus, one subject of the invention is a cosmetic composition comprising:
one or more non-nitrogenous zinc salts, and
one or more starches,
in a weight ratio of the amount of starch to the amount of zinc element ranging from 0.01 to 25.

Another subject of the present invention consists of a cosmetic process for treating keratin fibres, preferably human keratin fibres such as the hair, in which a composition according to the invention is applied to the keratin fibres and/or the scalp.

Another subject of the present invention concerns the use of a composition according to the invention, preferably in the form of a leave-on care product such as a hair conditioner, for conditioning keratin fibres, preferably human keratin fibres such as the hair, and for protecting their artificial colour from fading of the colours.

Other subjects, characteristics, aspects and advantages of the invention will emerge even more clearly on reading the description and the examples that follow.

The composition according to the invention is preferably a leave-on composition, and in particular a composition preferably comprising less than 3% by weight, more preferentially less than 1% by weight and better still no anionic, nonionic, amphoteric or zwitterionic surfactants, relative to the total weight of the composition.

The term "non-nitrogenous zinc salt" means any mineral or organic compound comprising in its structure at least one zinc-based cation and an anion derived from a mineral or organic acid, the said salt not comprising any nitrogen atoms in its structure.

The zinc salt(s) are chosen from water-soluble zinc salts, especially mineral and organic zinc salts, and mixtures thereof.

The term "water-soluble zinc salt" means any salt with a solubility in water of greater than or equal to 0.5% by weight, at a temperature of 25° C.

Among the water-soluble zinc salts that may be used according to the present invention, mention may be made of zinc sulfate, zinc chloride, zinc lactate, zinc gluconate, zinc phenolsulfonate, zinc citrate and zinc salicylate, derivatives thereof, and mixtures thereof.

The zinc salicylate and derivatives thereof according to the invention correspond to the following formula:

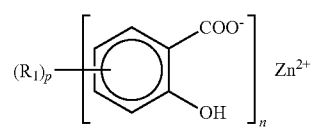

in which:
n=2 and p=0, 1, 2 or 3; and
$R_1$ denotes a linear or branched $C_1$-$C_{18}$ alkyl group (for example methyl, ethyl, n-propyl, isopropyl or n-butyl); a linear or branched $C_1$-$C_{18}$ hydroxyalkyl group; a halogen atom (for example iodine, bromine or chlorine); a $C_2$-$C_{18}$ acyl group (for example acetyl); a group $COR_2$ or $OCOR_2$, or $CONHR_2$, in which $R_2$ denotes a hydrogen atom or a linear or branched $C_1$-$C_{18}$ alkyl group.

Preferentially, zinc salt(s) are chosen from zinc sulfate, zinc chloride, zinc lactate, zinc gluconate, zinc salicylate and zinc citrate, and mixtures thereof.

Better still, the zinc salt(s) are chosen from zinc sulfate, zinc chloride, zinc lactate and zinc gluconate, alone or as a mixture.

Even more preferentially, the zinc salt is an organic zinc salt. Even more preferentially, the zinc salt is zinc lactate or zinc gluconate; better still, the zinc salt is zinc gluconate. Zinc gluconate is sold, for example, under the name Givobio G Zn by the company SEPPIC.

The composition of the invention preferably comprises from 0.1% to 10% by weight and in particular from 0.5% to 6.5% by weight of zinc salt(s) relative to the total weight of the composition.

The concentration of zinc element is preferably less than 2% by weight, in particular ranging from 0.005% to 1.5% by weight and better still from 0.1% to 1% by weight relative to the total weight of the composition.

The starches that may be used in the present invention are more particularly macromolecules in the form of polymers formed from elemental units that are anhydroglucose units. The number of these units and their assembly make it possible to distinguish amylose (linear polymer) and amylopectin (branched polymer). The relative proportions of amylose and of amylopectin, and their degree of polymerization, vary as a function of the plant origin of the starches.

The starch molecules used in the present invention may originate from a plant source such as cereals, tubers, roots, legumes and fruit. Thus, the starch(es) may originate from a plant source chosen from corn, pea, potato, sweet potato, banana, barley, wheat, rice, oat, sago, tapioca and sorghum. The starch is preferably derived from potato.

It is also possible to use the starch hydrolysates mentioned above.

Starches are generally in the form of a white powder, which is insoluble in cold water, whose elemental particle size ranges from 3 to 100 microns.

The starches used in the composition of the invention may be chemically modified via one or more of the following reactions: pregelatinization, oxidation, crosslinking, esterification, heat treatments.

More particularly, these reactions may be performed in the following manner:
pregelatinization by splitting the starch granules (for example drying and cooking in a drying drum);
oxidation with strong oxidizing agents, leading to the introduction of carboxyl groups into the starch molecule and to depolymerization of the starch molecule (for example by treating an aqueous starch solution with sodium hypochlorite);
crosslinking with functional agents capable of reacting with the hydroxyl groups of the starch molecules, which will thus bond together (for example with glyceryl and/or phosphate groups);
esterification in alkaline medium for the grafting of functional groups, especially $C_1$-$C_6$ acyl (acetyl), $C_1$-$C_6$ hydroxyalkyl (hydroxyethyl or hydroxypropyl), carboxy alkyl (in particular carboxymethyl) or octenylsuccinic. Mention is made in particular of starches modified with sodium carboxymethyl.

Monostarch phosphates (of the type Am—O—PO—$(OX)_2$), distarch phosphates (of the type Am—O—PO—(OX)—O—Am) or even tristarch phosphates (of the type Am—O—PO—(O—Am)$_2$) or mixtures thereof (Am meaning starch) may especially be obtained by crosslinking with phosphorus compounds.

X especially denotes alkali metals (for example sodium or potassium), alkaline-earth metals (for example calcium or magnesium), ammonium salts, amine salts, for instance those of monoethanolamine, diethanolamine, triethanolamine, 3-amino-1,2-propanediol, or ammonium salts derived from basic amino acids such as lysine, arginine, sarcosine, ornithine or citrulline.

The phosphorus compounds may be, for example, sodium tripolyphosphate, sodium orthophosphate, phosphorus oxychloride or sodium trimetaphosphate.

Starch phosphates, in particular hydroxypropyl starch phosphates, or compounds rich in starch phosphate and in particular in hydroxypropyl starch phosphate will preferentially be used, for instance the products sold under the references Prejel VA-70-T AGGL (gelatinized hydroxypropyl cassava distarch phosphate), Prejel TK1 (gelatinized cassava distarch phosphate) and Prejel 200 (gelatinized acetyl cassava distarch phosphate) by the company Avebe, or Structure Zea from National Starch (gelatinized hydroxypropyl corn distarch phosphate).

When the starches are chemically modified via an esterification reaction, carboxyalkyl starches as indicated previously are obtained.

The carboxyalkyl starches are preferably carboxy($C_1$-$C_4$) alkyl starch and more particularly carboxymethyl starches.

The salts are especially salts of alkali metals or alkaline-earth metals such as Na, K ½, Li, $NH_4$, or salts of a quaternary ammonium or of an organic amine such as monoethanolamine, diethanolamine or triethanolamine.

Carboxyalkyl starches are obtained by grafting carboxyalkyl groups onto one or more alcohol functions of starch, especially by reaction of starch and of sodium monochloroacetate in alkaline medium.

The carboxyalkyl groups are generally attached via an ether function, more particularly to carbon 1.

The degree of substitution preferably ranges from 0.1 to 1 and more particularly from 0.15 to 0.5. The degree of substitution is defined according to the present invention as being the mean number of hydroxyl groups substituted with an ester or ether group (in the present case ether for the carboxymethyl starches) per monosaccharide unit of the polysaccharide.

The carboxyalkyl starches preferably comprise units having the following formula:

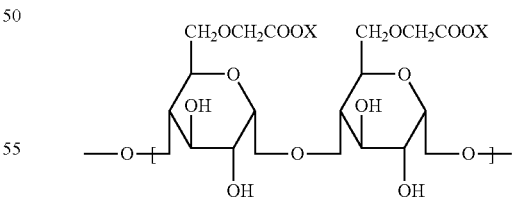

X denotes a hydrogen atom, an alkali metal or alkaline-earth metal such as Na, K ½, Li or $NH_4$, a quaternary ammonium or an organic amine. Preferably, X denotes an ion $Na^+$.

The carboxyalkyl starches that may be used according to the present invention are preferably non-pregelatinized carboxyalkyl starches.

The carboxyalkyl starches that may be used according to the present invention are preferably partially or totally crosslinked carboxyalkyl starches.

The carboxyalkyl starches that may be used according to the present invention are preferably sodium salts of carboxyalkyl starches, in particular a sodium salt of potato carboxymethyl starch, sold especially under the name Primojel by the company DMV International. More than 95% of the particles of this starch have a diameter of less than 100 microns and more particularly less than 65 microns.

According to the invention, it is also possible to use amphoteric starches, these amphoteric starches containing one or more anionic groups and one or more cationic groups. The anionic and cationic groups may be linked to the same reactive site of the starch molecule or to different reactive sites; they are preferably linked to the same reactive site. The anionic groups may be of carboxylic, phosphate or sulfate type, preferably carboxylic. The cationic groups may be of primary, secondary, tertiary or quaternary amine type.

The amphoteric starches are especially chosen from the compounds having the following formulae:

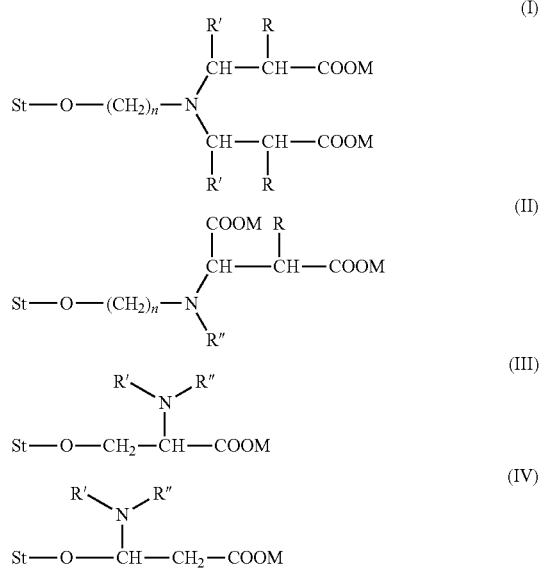

in which formulae:
St-O represents a starch molecule,
R, which may be identical or different, represents a hydrogen atom or a methyl radical,
R', which may be identical or different, represents a hydrogen atom, a methyl radical or a —COOH group,
n is an integer equal to 2 or 3,
M, which may be identical or different, denotes a hydrogen atom, an alkali metal or alkaline-earth metal such as Na, K, Li or $NH_4$, a quaternary ammonium or an organic amine,
R" represents a hydrogen atom or an alkyl radical containing from 1 to 18 carbon atoms.

These compounds are especially described in patents U.S. Pat. Nos. 5,455,340 and 4,017,460.

The starches of formula (I) or (II) are particularly used as amphoteric starches. Starches modified with 2-chloroethylaminodipropionic acid are more particularly used, i.e. starches of formula (I) or (II) in which R, R', R" and M represent a hydrogen atom and n is equal to 2. Mention may be made in particular of the potato starch modified with 2-chloroethylaminodipropionic acid neutralized with sodium hydroxide, sold under the reference Structure Solanace by the company National Starch.

Preferably, the starch(es) that may be used in the invention are chemically modified.

Even more preferentially, optionally hydroxypropylated starch phosphates be used as starches.

The starch(es) present in the composition generally represent from 0.01% to 15%, preferably from 1% to 10% and better still from 2% to 8% by weight relative to the total weight of the composition.

The weight ratio of the amount of starch to the amount of zinc element ranges from 0.01 to 25, preferably from 0.05 to 20 and better still from 1 to 15.

The composition according to the invention may comprise one or more additives chosen from fatty alcohols, fatty esters, cationic polymers, cationic surfactants and silicones, and mixtures thereof.

The composition according to the invention may thus comprise one or more esters of fatty alcohol and/or of fatty acid and preferably of saturated fatty acid and of saturated fatty monoalcohol.

The fatty esters used in the composition of the invention are saturated fatty acid esters, i.e. esters of saturated carboxylic acids comprising at least 10 carbon atoms, and of saturated fatty monoalcohols comprising at least 10 carbon atoms.

The saturated acids or monoalcohols may be linear or branched. The saturated carboxylic acids preferably comprise from 10 to 30 carbon atoms and more preferentially from 12 to 24 carbon atoms. They may optionally be hydroxylated. The saturated fatty monoalcohols preferably comprise from 10 to 30 carbon atoms and more particularly from 12 to 24 carbon atoms. Preferably, the fatty esters of the invention are solid at 25° C. and at atmospheric pressure.

Preferably, the fatty esters are chosen from myristyl myristate, cetyl myristate, stearyl myristate, myristyl palmitate, cetyl palmitate, stearyl palmitate, myristyl stearate, cetyl stearate, stearyl stearate and behenyl behenate, and mixtures thereof.

The composition according to the invention preferably comprises from 0.01% to 10% and better still from 0.1% to 5% by weight of fatty alcohol or fatty acid ester(s) relative to the total weight of the composition.

The composition according to the invention may also comprise one or more fatty alcohols.

For the purposes of the present invention, the term "fatty alcohol" means any saturated or unsaturated, linear or branched pure fatty alcohol comprising at least 8 carbon atoms and not comprising any oxyalkylene or glycerol groups.

The fatty alcohol may have the structure R—OH in which R denotes a saturated or unsaturated, linear or branched radical containing from 8 to 40 and preferably from 8 to 30 carbon atoms; R preferably denotes a $C_{12}$-$C_{24}$ alkyl or $C_{12}$-$C_{24}$ alkenyl group. R may be substituted with one or more hydroxyl groups.

Examples of fatty alcohols that may be mentioned include lauryl alcohol, myristyl alcohol, cetyl alcohol, dodecyl alcohol, decyl alcohol, stearyl alcohol, oleyl alcohol, behenyl alcohol, linoleyl alcohol, undecylenyl alcohol, palmitoleyl alcohol, arachidonyl alcohol and erucyl alcohol, and mixtures thereof.

The fatty alcohol may represent a mixture of fatty alcohols, which means that several species of fatty alcohol may coexist, in the form of a mixture, in a commercial product.

Fatty alcohol mixtures that may be mentioned include cetylstearyl alcohol and cetearyl alcohol.

Among all the fatty alcohols that may be used according to the invention, used is preferably made of one or more fatty alcohols chosen from cetyl alcohol, stearyl alcohol and myristyl alcohol, or mixtures thereof.

When they are present, the composition according to the invention preferably comprises from 0.1% to 10% and better still from 1% to 5% by weight of fatty alcohol(s) relative to the total weight of the composition.

The composition according to the invention may also comprise one or more cationic surfactants chosen from the following quaternary ammonium salts:

the quaternary ammonium salts of formula (V) below:

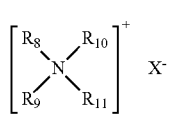

(V)

in which the radicals $R_8$ to $R_{11}$, which may be identical or different, represent an aromatic radical such as aryl or alkylaryl or a linear or branched aliphatic radical comprising from 1 to 30 carbon atoms, at least one of the radicals $R_8$ to $R_{10}$ comprising an alkyl or alkenyl radical comprising from 8 to 30 carbon atoms, preferably from 14 to 30 carbon atoms and better still from 16 to 25 carbon atoms, the aliphatic radicals possibly comprising heteroatoms especially such as oxygen, nitrogen, sulfur and halogens.

The aliphatic radicals are, for example, chosen from alkyl, alkoxy, polyoxy($C_2$-$C_6$)alkylene, alkylamide, ($C_{12}$-$C_{22}$)alkylamido($C_2$-$C_6$)alkyl, ($C_{12}$-$C_{22}$)alkyl acetate or hydroxyalkyl radicals comprising approximately from 1 to 30 carbon atoms, preferably from 14 to 30 and better still from 16 to 25 carbon atoms; $X^-$ is an anion chosen from the group of the halides, phosphates, acetates, lactates, ($C_2$-$C_6$)alkyl sulfates, or alkyl- or alkylaryl-sulfonates such as methosulfate;

Among the quaternary ammonium salts of formula (I), it is preferred to use alkyltrimethylammonium chlorides in which the alkyl radical comprises from about 12 to 22 carbon atoms, in particular behenyltrimethylammonium or cetyltrimethylammonium salts or oleocetyldimethylhydroxyethylammonium salts.

quaternary ammonium salts of imidazoline, for instance those of formula (VI) below:

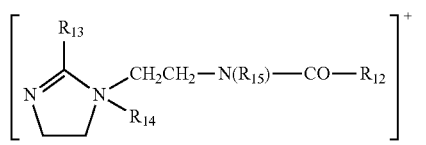

(VI)

in which $R_{12}$ represents an alkyl or alkenyl group comprising from 8 to 30 carbon atoms, for example fatty acid derivatives of tallow, $R_{13}$ represents a hydrogen atom, a $C_1$-$C_4$ alkyl group or an alkyl or alkenyl group comprising from 8 to 30 carbon atoms, $R_{14}$ represents a $C_1$-$C_4$ alkyl group, $R_{15}$ represents a hydrogen atom or a $C_1$-$C_4$ alkyl group, $X^-$ is an anion chosen from the group of halides, phosphates, acetates, lactates, ($C_1$-$C_4$)alkyl sulfates and ($C_1$-$C_4$)alkyl- or ($C_1$-$C_4$)alkylaryl-sulfonates. $R_{12}$ and $R_{13}$ preferably denote a mixture of alkyl or alkenyl groups comprising from 12 to 21 carbon atoms, for example tallow fatty acid derivatives, $R_{14}$ denotes a methyl group, and $R_{15}$ denotes a hydrogen atom. Such a product is, for example, sold under the name Rewoquat® W 75 by the company Rewo, quaternary diammonium or triammonium salts, particularly of formula (VII) below:

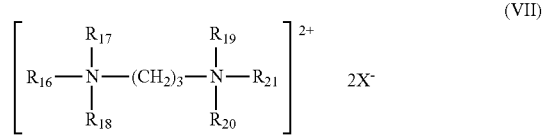

(VII)

in which $R_{16}$ denotes an alkyl group comprising for about 16 to 30 carbon atoms, optionally hydroxylated and/or interrupted with one or more oxygen atoms; $R_{17}$ is chosen from hydrogen, an alkyl group comprising from 1 to 4 carbon atoms or a group $-(CH_2)_3-N^+(R_{16a})(R_{17a})(R_{18a})$; $R_{16a}$, $R_{17a}$, $R_{18a}$, $R_{18}$, $R_{19}$, $R_{20}$ and $R_{21}$, which may be identical or different, are chosen from hydrogen and an alkyl group comprising from 1 to 4 carbon atoms, and $X^-$ is an anion chosen from the group of halides, acetates, phosphates, nitrates, ($C_1$-$C_4$)alkyl sulfates and ($C_1$-$C_4$)alkyl- or ($C_1$-$C_4$)alkylaryl-sulfonates, in particular methyl sulfate and ethyl sulfate. Such compounds are, for example, Finquat CT-P, sold by the company Finetex (Quaternium 89), and Finquat CT, sold by the company Finetex (Quaternium 75);

quaternary ammonium salts containing one or more ester functions, for instance those of formula (VIII) below:

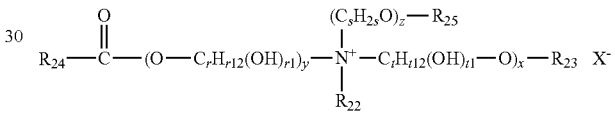

in which:
$R_{22}$ is chosen from $C_1$-$C_6$ alkyl and $C_1$-$C_6$ hydroxyalkyl or dihydroxyalkyl groups;
$R_{23}$ is chosen from:
  the group $R_{26}-C(O)-$,
  linear or branched, saturated or unsaturated $C_1$-$C_{22}$ hydrocarbon-based groups $R_{27}$,
  a hydrogen atom,
$R_{25}$ is chosen from:
  the group $R_{28}-C(O)-$,
  linear or branched, saturated or unsaturated $C_1$-$C_6$ hydrocarbon-based groups $R_{29}$,
  a hydrogen atom,
$R_{24}$, $R_{26}$ and $R_{28}$, which may be identical or different, are chosen from linear or branched, saturated or unsaturated $C_7$-$C_{21}$ hydrocarbon-based groups;
s and t, which may be identical or different, are integers ranging from 2 to 6,
r1 and t1, which may be identical or different, are equal to 0 or 1,
r2+r1=2r and t1+t2=2t,
y is an integer ranging from 1 to 10,
x and z, which may be identical or different, are integers ranging from 0 to 10,
$X^-$ is a simple or complex, organic or mineral anion,
with the proviso that the sum x+y+z is from 1 to 15, that when x is 0, then $R_{23}$ denotes $R_{27}$ and that when z is 0, then $R_{25}$ denotes $R_{29}$.

The alkyl groups $R_{22}$ may be linear or branched, and more particularly linear.

Preferably, $R_{22}$ denotes a methyl, ethyl, hydroxyethyl or dihydroxypropyl group, and more particularly a methyl or ethyl group.

Advantageously, the sum x+y+z is from 1 to 10.

When $R_{23}$ is a hydrocarbon-based group $R_{27}$, it may be long and contain from 12 to 22 carbon atoms, or may be short and contain from 1 to 3 carbon atoms.

When $R_{25}$ is a hydrocarbon-based group $R_{29}$, it preferably contains 1 to 3 carbon atoms.

Advantageously, $R_{24}$, $R_{26}$ and $R_{28}$, which may be identical or different, are chosen from linear or branched, saturated or unsaturated $C_{11}$-$C_{21}$ hydrocarbon-based groups, and more particularly from linear or branched, saturated or unsaturated $C_{11}$-$C_{21}$ alkyl and alkenyl groups.

Preferably, x and z, which may be identical or different, are equal to 0 or 1.

Advantageously, y is equal to 1.

Preferably, r, s and t, which may be identical or different, are equal to 2 or 3, and even more particularly are equal to 2.

The anion $X^-$ is preferably a halide, preferably chloride, bromide or iodide, a ($C_1$-$C_4$)alkyl sulfate or a ($C_1$-$C_4$)alkyl- or ($C_1$-$C_4$)alkylaryl-sulfonate. However, it is possible to use methanesulfonate, phosphate, nitrate, tosylate, an anion derived from an organic acid, such as acetate or lactate, or any other anion that is compatible with the ammonium containing an ester function.

The anion $X^-$ is even more particularly chloride, methyl sulfate or ethyl sulfate.

Use is made more particularly, in the composition according to the invention, of the ammonium salts of formula (VIII) in which:

$R_{22}$ denotes a methyl or ethyl group, x and y are equal to 1, z is equal to 0 or 1, r, s and t are equal to 2, $R_{23}$ is chosen from a hydrogen atom, methyl, ethyl or $C_{14}$-$C_{22}$ hydrocarbon-based groups, and the group $R_{26}$—C(O)—, $R_{25}$ is chosen from a hydrogen atom and the group $R_{28}$—C(O)—;

$R_{24}$, $R_{26}$ and $R_{28}$, which may be identical or different, are chosen from linear or branched, saturated or unsaturated $C_{13}$-$C_{17}$ hydrocarbon-based groups, and more particularly from linear or branched, saturated or unsaturated $C_{13}$-$C_{17}$ alkyl and alkenyl groups.

Advantageously, the hydrocarbon-based radicals are linear.

Among the compounds of formula (VIII), examples that may be mentioned include salts, especially the chloride or methyl sulfate, of diacyloxy-ethyldimethylammonium, diacyloxyethylhydroxyethylmethylammonium, monoacyl-oxyethyldihydroxyethylmethylammonium, triacyloxyethylmethylammonium or monoacyloxyethylhydroxyethyldimethylammonium, and mixtures thereof. The acyl groups preferably contain 14 to 18 carbon atoms and are obtained more particularly from a plant oil such as palm oil or sunflower oil. When the compound contains several acyl groups, these groups may be identical or different.

These products are obtained, for example, by direct esterification of triethanolamine, triisopropanolamine, an alkyldiethanolamine or an alkyldiisopropanolamine, which are optionally oxyalkylenated, with fatty acids or with fatty acid mixtures of plant or animal origin, or by transesterification of the methyl esters thereof. This esterification is followed by a quaternization by means of an alkylating agent such as an alkyl halide, preferably methyl or ethyl halide, a dialkyl sulfate, preferably methyl or ethyl sulfate, methyl methanesulfonate, methyl para-toluenesulfonate, glycol chlorohydrin or glycerol chlorohydrin.

Such compounds are, for example, sold under the names Dehyquart® by Henkel, Stepanquat® by Stepan, Noxamium® by Ceca or Rewoquat® WE 18 by Rewo-Witco.

The composition according to the invention may contain, for example, a mixture of quaternary ammonium salts of mono-, di- and triesters with a weight majority of diester salts.

It is also possible to use the ammonium salts containing at least one ester function that are described in patents U.S. Pat. Nos. 4,874,554 and 4,137,180.

Use may be made of behenoylhydroxypropyltrimethylammonium chloride sold by Kao under the name Quartamin BTC 131.

Preferably, the ammonium salts containing at least one ester function contain two ester functions.

Among the cationic surfactants that may be present in the composition according to the invention, it is more particularly preferred to choose cetyltrimethylammonium, behenyltrimethylammonium and dipalmitoylethyl-hydroxyethylmethylammonium salts, and mixtures thereof, and more particularly behenyltrimethylammonium chloride, cetyltrimethylammonium chloride, and dipalmitoylethylhydroxyethylammonium methosulfate, and mixtures thereof.

When they are present, the amount of the cationic surfactant(s) preferably ranges from 0.01% to 20% by weight and better still from 0.2% to 10% by weight, relative to the total weight of the composition.

The cationic surfactant(s) that may be used according to the invention are present in amounts preferably ranging from 0.01% to 10% by weight, in particular from 0.05% to 5% by weight and better still from 0.1% to 3% by weight, relative to the total weight of the composition.

The composition according to the invention may also comprise one or more non-silicone cationic polymers.

The cationic polymer(s) that may be used in accordance with the present invention may be selected from all of those already known per se to enhance the cosmetic properties of hair treated with detergent compositions, these being, in particular, the polymers described in patent application EP-A-0 337 354 and in French patent applications FR-A-2 270 846, 2 383 660, 2 598 611, 2 470 596, 2 519 863 and 2 875 503.

The preferred cationic polymer(s) are chosen from those that contain in their structure units comprising primary, secondary, tertiary and/or quaternary amine groups that may either form part of the main polymer chain or may be borne by a side substituent directly attached thereto.

Among the cationic polymers that may be mentioned more particularly are polymers of the polyamine, polyaminoamide and polyquaternary ammonium type. Among these polymers, mention may be made of:

(1) Homopolymers or copolymers derived from crosslinked or non-crosslinked acrylic or methacrylic esters or amides and comprising at least one of the units of formula (IX), (X), (XI) or (XII) below:

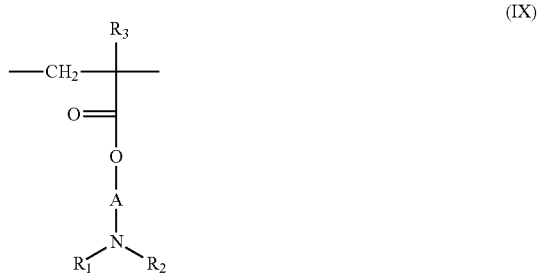

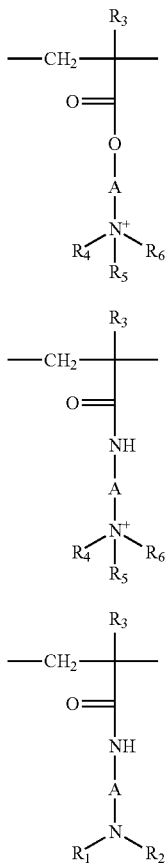

in which
R$_1$ and R$_2$, which are identical or different, each represent a hydrogen atom or an alkyl group having from 1 to 6 carbon atoms, and preferably methyl or ethyl;

R$_3$, which may be identical or different, each denote a hydrogen atom or a group CH$_3$;

A, which may be identical or different, each represent a linear or branched alkyl group of 1 to 6 carbon atoms, preferably 2 or 3 carbon atoms, or a hydroxyalkyl group of 1 to 4 carbon atoms;

R$_4$, R$_5$, R$_6$, which may be identical or different, each represent an alkyl group containing from 1 to 6 carbon atoms or a benzyl group, and preferably an alkyl group containing from 1 to 6 carbon atoms;

X$^-$ denotes an anion derived from a mineral or organic acid, such as a methosulfate anion or a halide such as chloride or bromide.

The polymers of family (1) can also contain one or more units derived from comonomers which may be chosen from the family of acrylamides, methacrylamides, diacetone acrylamides, acrylamides and methacrylamides substituted on the nitrogen with lower (C$_1$-C$_4$) alkyls, acrylic or methacrylic acids or esters thereof, vinyllactams such as vinylpyrrolidone or vinylcaprolactam, and vinyl esters.

Thus, among these polymers of family (1), mention may be made of:
copolymers of acrylamide and of dimethylaminoethyl methacrylate quaternized with dimethyl sulfate or with a dimethyl halide, such as the product sold under the name Hercofloc by the company Hercules,
copolymers of acrylamide and of methacryloyloxyethyltrimethylammonium chloride which are described, for example, in patent application EP-A-080976 and are sold under the name Bina Quat P 100 by the company Ciba Geigy,
the copolymer of acrylamide and of methacryloyloxyethyltrimethylammonium methosulfate sold under the name Reten by the company Hercules,
quaternized or non-quaternized vinylpyrrolidone/dialkylaminoalkyl acrylate or methacrylate copolymers, such as the products sold under the name Gafquat by the company ISP, such as, for example, Gafquat 734 or Gafquat 755 (Polyquaternium-11), or alternatively the products known as Copolymer 845, 958 and 937. These polymers are described in detail in French patents 2 077 143 and 2 393 573. Polyquaternium-11 is preferably used.
dimethylaminoethyl methacrylate/vinylcaprolactam/vinylpyrrolidone terpolymers, such as the product sold under the name Gaffix VC 713 by the company ISP,
vinylpyrrolidone/methacrylamidopropyldimethylamine copolymers sold in particular under the name Styleze CC 10 by ISP, and
quaternized vinylpyrrolidone/dimethylaminopropylmethacrylamide copolymers such as the product sold under the name Gafquat HS 100 by the company ISP, and
the crosslinked polymers of methacryloyloxy(C$_1$-C$_4$)alkyl tri(C$_1$-C$_4$)alkylammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with an olefinically unsaturated compound, more particularly methylenebisacrylamide. A crosslinked acrylamide/methacryloyloxyethyltrimethyl-ammonium chloride copolymer (20/80 by weight) in the form of a dispersion containing 50% by weight of the said copolymer in mineral oil can be used more particularly. This dispersion is sold under the name Salcare® SC 92 by the company Ciba. Use may also be made of a crosslinked homopolymer of methacryloyloxyethyltrimethylammonium chloride containing approximately 50% by weight of the homopolymer in mineral oil or in a liquid ester. These dispersions are sold under the names Salcare® SC 95 and Salcare® SC 96 by the company Ciba.

(2) Cationic polysaccharides chosen especially from:
a) cellulose ether derivatives comprising quaternary ammonium groups described in French patent 1 492 597, and in particular the polymers sold under the names "JR" (JR 400, JR 125, JR 30M) or "LR" (LR 400, LR 30M) by the company Union Carbide Corporation. These polymers are also defined in the CTFA dictionary as quaternary ammoniums of hydroxyethylcellulose that have reacted with an epoxide substituted with a trimethylammonium group.
b) cellulose copolymers or cellulose derivatives grafted with a water-soluble quaternary ammonium monomer, such as hydroxyalkyl celluloses, for instance hydroxymethyl, hydroxyethyl or hydroxypropyl celluloses grafted especially with a methacryloylethyltrimethylammonium, methacrylamidopropyltrimethylammonium or dimethyldiallylammonium salt.

The commercial products corresponding to this definition are more particularly the products corresponding to the INCI name Polyquaternium-4, sold under the names Celquat L 200 and Celquat H 100 by the company National Starch or Celquat LOR by the company Akzo Nobel.
c) Guar gums containing trialkylammonium cationic groups. Use is made, for example, of guar gums modified with a 2,3-epoxypropyltrimethylammonium salt (for example, chloride).

Such products are sold in particular under the trade names Jaguar C13 S, Jaguar C 15, Jaguar C 17 or Jaguar C162 by the company Meyhall.

(3) Polymers formed from piperazinyl units and divalent alkylene or hydroxyalkylene radicals containing straight or branched chains, optionally interrupted with oxygen, sulfur or nitrogen atoms or with aromatic or heterocyclic rings, and also the oxidation and/or quaternization products of these polymers. Such polymers are described, in particular, in French patents 2 162 025 and 2 280 361.

(4) Water-soluble cationic polyaminoamides, prepared in particular by polycondensation of an acid compound with a polyamine; these polyaminoamides may be crosslinked with an epihalohydrin, a diepoxide, a saturated or unsaturated dianhydride, a bis-unsaturated derivative, a bis-halohydrin, a bis-azetidinium, a bis-haloacyldiamine or a bis-alkyl halide or else by an oligomer resulting from the reaction of a bifunctional compound which is reactive towards a bis-halohydrin, a bis-azetidinium, a bis-haloacyldiamine, a bis-alkyl halide, an epihalohydrin, a diepoxide or a bis-unsaturated derivative; these polyaminoamides may be alkylated, or quaternized if they contain one or more tertiary amine functions. Such polymers are described, in particular, in French patents 2 252 840 and 2 368 508.

(5) Polyamino amide derivatives resulting from the condensation of polyalkylene polyamines with polycarboxylic acids followed by alkylation with difunctional agents. Mention may be made, for example, of adipic acid/dialkylaminohydroxy-alkyldialkylenetriamine polymers in which the alkyl radical comprises from 1 to 4 carbon atoms and preferably denotes methyl, ethyl or propyl. Such polymers are especially described in French patent 1 583 363.

Among these derivatives, mention may be made more particularly of the adipic acid/dimethylaminohydroxypropyl/diethylenetriamine polymers sold under the name Cartaretine F, F4 or F8 by the company Sandoz.

(6) Polymers obtained by reaction of a polyalkylene polyamine containing two primary amine groups and at least one secondary amine group with a dicarboxylic acid chosen from diglycolic acid and saturated aliphatic dicarboxylic acids having from 3 to 6 carbon atoms. The mole ratio between the polyalkylene polyamine and the dicarboxylic acid is between 0.8:1 and 1.4:1; the polyaminoamide resulting therefrom is reacted with epichlorohydrin in a molar ratio of epichlorohydrin relative to the secondary amine group of the polyaminoamide of between 0.5:1 and 1.8:1. Such polymers are described in particular in U.S. Pat. Nos. 3,227,615 and 2,961,347.

Polymers of this type are sold in particular under the name Hercosett 57 by the company Hercules Inc. or alternatively under the name PD 170 or Delsette 101 by the company Hercules in the case of the adipic acid/epoxypropyl/diethylenetriamine copolymer.

(7) Alkyldiallylamine or dialkyldiallylammonium cyclopolymers, such as the homopolymers or copolymers containing, as the main constituent of the chain, units conforming to the formula (XIII) or (XIV):

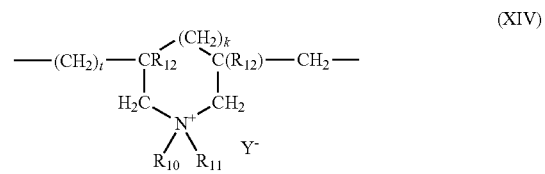

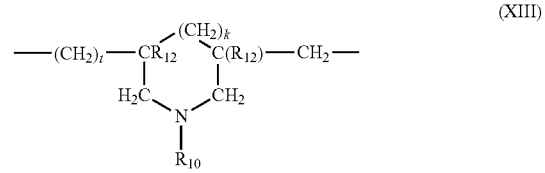

in which k and t are equal to 0 or 1, the sum k+t being equal to 1; $R_{12}$ denotes a hydrogen atom or a methyl group; $R_{10}$ and $R_{11}$, independently of one another, denote an alkyl group having from 1 to 6 carbon atoms, a hydroxyalkyl group in which the alkyl group has preferably 1 to 5 carbon atoms, a lower amidoalkyl group (i.e. the alkyl part of which is $C_1$-$C_4$), or else $R_{10}$ and $R_{11}$ may, together with the nitrogen atom to which they are attached, denote heterocyclic groups, such as piperidyl or morpholinyl; r is an anion such as bromide, chloride, acetate, borate, citrate, tartrate, bisulfate, bisulfite, sulfate or phosphate. These polymers are especially described in French patent 2 080 759 and in its Certificate of Addition 2 190 406.

$R_{10}$ and $R_{11}$, independently of one another, preferably denote an alkyl group containing from 1 to 4 carbon atoms.

Among the polymers defined above, mention may be made of dialkyldiallylammonium chloride homopolymers, more particularly dimethyldiallylammonium chloride homopolymer (INCI name: Polyquaternium-6) sold, for example, under the name Merquat® 100 by the company Nalco (and homologues thereof of low weight-average molecular masses) and dialkyldiallylammonium chloride homopolymers, more particularly the copolymer of dimethyldiallylammonium chloride and of acrylamide sold under the name Merquat® 550.

(8) The quaternary diammonium polymers containing repeating units corresponding to formula (XV):

in which:
$R_{13}$, $R_{14}$, $R_{15}$ and $R_{16}$, which may be identical or different, represent aliphatic, alicyclic or arylaliphatic groups containing from 1 to 6 carbon atoms or lower hydroxyalkylaliphatic groups (i.e. the alkyl part of which is $C_1$-$C_4$), or alternatively $R_{13}$, $R_{14}$, $R_{15}$ and $R_{16}$, together or separately, constitute, with the nitrogen atoms to which they are attached, heterocycles optionally containing a second heteroatom other than nitrogen, or alternatively $R_{13}$, $R_{14}$, $R_{15}$ and $R_{16}$ each represent a linear or branched $C_1$-$C_6$ alkyl group substituted with a nitrile, ester, acyl or amide group or a —CO—O—$R_{17}$-E or —CO—NH—$R_{17}$-E group where $R_{17}$ is an alkylene group and E is a quaternary ammonium group;
$A_1$ and $B_1$ represent polymethylene groups containing from 2 to 8 carbon atoms, which may be linear or branched and saturated or unsaturated and may contain, joined to or intercalated in the main chain, one or more aromatic rings, or one or more oxygen or sulfur atoms or sulfoxide, sulfone, disulfide, amino, alkylamino, hydroxyl, quaternary ammonium, ureido, amide or ester groups, and $X^-$ denotes an anion derived from a mineral or organic acid;

$A_1$ $R_{13}$ and $R_{15}$ may, with the two nitrogen atoms to which they are attached, form a piperazine ring; moreover, if $A_1$ denotes a linear or branched, saturated or unsaturated alkylene or hydroxyalkylene group, $B_1$ may also denote a group:

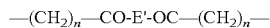
—(CH$_2$)$_n$—CO-E'-OC—(CH$_2$)$_n$— in which n denotes an integer from 0 to 7 and E' denotes:

a) a glycol residue of formula —O—Z—O—, in which Z denotes a linear or branched hydrocarbon group, or a group conforming to one of the following formulae:

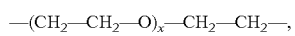
—(CH$_2$—CH$_2$—O)$_x$—CH$_2$—CH$_2$—,

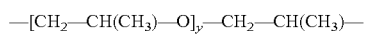
—[CH$_2$—CH(CH$_3$)—O]$_y$—CH$_2$—CH(CH$_3$)— in which x and y each denote an integer from 1 to 4, representing a defined and unique degree of polymerization or any number from 1 to 4 representing an average degree of polymerization, b) a bis-secondary diamine residue such as a piperazine derivative;

c) a bis-primary diamine residue of formula —NH—Y—NH—, in which Y denotes a linear or branched hydrocarbon-based group, or alternatively the divalent group —CH$_2$—CH$_2$—S—S—CH$_2$—CH$_2$—;

d) a ureylene group of formula —NH—CO—NH—.

Preferably, $X^-$ is an anion such as chloride or bromide.

Polymers of this type are described in particular in French patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

Use may be made more particularly of polymers that are formed from repeating units corresponding to formula (XVI):

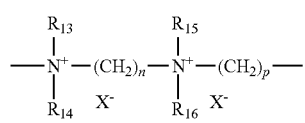
(XVI)

in which $R_{13}$, $R_{14}$, $R_{15}$ and $R_{16}$, which may be identical or different, each denote an alkyl or hydroxyalkyl group having from 1 to 4 carbon atoms approximately, n and p are integers ranging from 2 to 8 approximately, and $X^-$ is an anion derived from a mineral or organic acid. Preferably, $R_{13}$, $R_{14}$, $R_{15}$ and $R_{16}$ each denote a methyl group. As an example of a polymer that may be used corresponding to formula (XVI), mention may be made of hexadimethrine chloride, sold under the name Mexomer PO by the company Chimex.

(9) Polyquaternary ammonium polymers composed of units of formula (XVII):

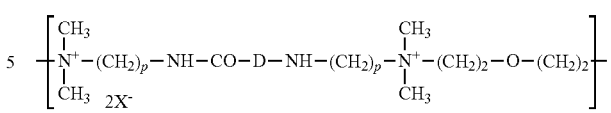
(XVII)

in which:

p denotes an integer ranging from 1 to 6 approximately,

D may be nothing or may represent a group
—(CH$_2$)$_r$—CO— in which r denotes a number equal to 4 or 7, and $X^-$ denotes an anion derived from a mineral or organic acid.

Cationic polymers comprising units of formula (XVII) are especially described in patent application EP-A-122 324 and may be prepared according to the processes described in U.S. Pat. Nos. 4,157,388, 4,390,689, 4,702,906 and 4,719,282.

Among these polymers, the ones that are preferred are those with a molecular mass, measured by carbon-13 NMR, of less than 100 000, and in the formula of which:

p is equal to 3, and a) D represents a group —(CH$_2$)$_4$—CO—, X denotes a chlorine atom, the molecular mass measured by carbon-13 NMR ($^{13}$C NMR) being about 5600; a polymer of this type is sold by the company Miranol under the name Mirapol-AD1, b) D represents a group —(CH$_2$)$_7$—CO—, X denotes a chlorine atom, the molecular mass measured by carbon-13 NMR ($^{13}$C NMR) being about 8100; a polymer of this type is sold by the company Miranol under the name Mirapol-AZ1, c) D denotes the value zero, X denotes a chlorine atom, the molecular mass measured by carbon-13 NMR ($^{13}$C NMR) being about 25 500; a polymer of this type is sold by the company Miranol under the name Mirapol-A15, d) a "block copolymer" formed from units corresponding to the polymers described in paragraphs a) and c), sold by the company Miranol under the names Mirapol-9 ($^{13}$C NMR molecular mass of about 7800), Mirapol-175 ($^{13}$C NMR molecular mass of about 8000) and Mirapol-95 ($^{13}$C NMR molecular mass of about 12 500). Even more particularly, the polymer containing units of formula (XVII) in which p is equal to 3, D denotes the value zero and X denotes a chlorine atom, the molecular mass measured by carbon-13 NMR ($^{13}$C NMR) being about 25 500, is preferred according to the invention.

(10) Quaternary polymers of vinylpyrrolidone and of vinylimidazole, for instance the products sold under the names Luviquat FC 905, FC 550 and FC 370 by the company BASF.

(11) Cationic polyamines such as Polyquart H sold by Henkel, referred to under the name polyethylene glycol (15) tallow polyamine in the CTFA dictionary.

(12) Vinylamide homopolymers or copolymers and in particular partially hydrolysed vinylamide homopolymers such as poly(vinylamine/vinylamide)s. These polymers are formed from at least one vinylamide monomer corresponding to the following formula:

H$_2$C=CR$^2$NRC(O)R$^1$ in which R, $R^1$ and $R^2$ are each chosen from a hydrogen atom, a $C_1$-$C_{20}$ alkyl group, an aryl group and an alkylaryl group in which the alkyl part comprises from 1 to 20 carbon atoms.

In particular, the said monomer may be chosen from N-vinylformamide, N-methyl-N-vinylacetamide and N-vinylacetamide. Preferably, poly(vinylamine/N-vinylformamide) is used, as sold under the name Catiofast VMP by the company BASF or under the name Lupamin 9030 by the company BASF.

These polymers may be formed, for example, by radical polymerization of a vinylamide monomer followed by partial acidic or basic hydrolysis of the amide functions to quaternizable amine functions, as described in patent applications WO 2007/005 577, U.S. Pat. Nos. 5,374,334, 6,426,383 and 6,894,110.

(13) Cationic polyurethanes;

(14) Other cationic polymers that may be used in the context of the invention are cationic proteins or cationic protein hydrolysates, polyalkyleneimines, in particular polyethyleneimines, polymers containing vinylpyridine or vinylpyridinium units, and chitin derivatives.

Among all the cationic polymers that may be used in the context of the present invention, it is preferred to use the polymers of families (1), (2) and (7) and in particular copolymers of hydroxyethylcellulose and of diallyldimethylammonium chloride (Polyquaternium-4) or Polyquaternium-11 in the composition according to the invention.

When they are present, the composition according to the invention may comprise from 0.001% to 5% by weight and in particular from 0.01% to 2% by weight of cationic polymer(s) relative to the total weight of the composition.

The composition according to the invention may also comprise a silicone, preferably an amino silicone.

For the purposes of the present invention, the term "amino silicone" means any silicone comprising at least one primary, secondary or tertiary amine function or a quaternary ammonium group.

The amino silicones used in the cosmetic composition according to the present invention are chosen from:

(a) the compounds corresponding to formula (XVIII) below:

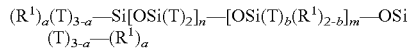

in which:

T is a hydrogen atom or a phenyl, hydroxyl (—OH) or $C_1$-$C_8$ alkyl radical, and preferably methyl, or a $C_1$-$C_8$ alkoxy, preferably methoxy, a denotes the number 0 or an integer from 1 to 3, and preferably 0, b denotes 0 or 1, and in particular 1, m and n are numbers such that the sum (n+m) can range especially from 1 to 2000 and in particular from 50 to 150, it being possible for n to denote a number from 0 to 1999 and in particular from 49 to 149, and for m to denote a number from 1 to 2000 and in particular from 1 to 10;

$R^1$ is a monovalent radical of formula —$C_qH_{2q}$L in which q is a number from 2 to 8 and L is an optionally quaternized amino group chosen from the following groups:

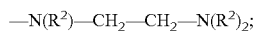

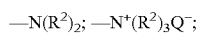

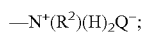

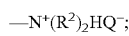

in which $R^2$ can denote a hydrogen atom, a phenyl, a benzyl or a saturated monovalent hydrocarbon-based radical, for example a $C_1$-$C_{20}$ alkyl radical, and $Q^-$ represents a halide ion such as, for example, fluoride, chloride, bromide or iodide. In particular, the amino silicones corresponding to the definition of formula (XVIII) are chosen from the compounds corresponding to formula (XIX) below:

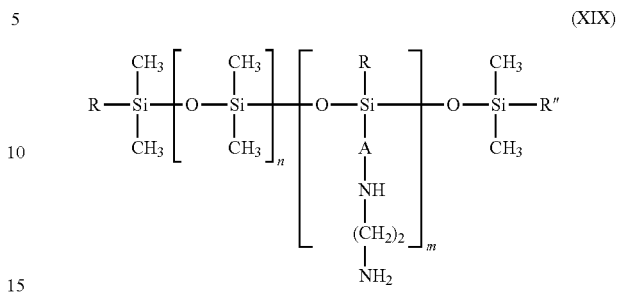

in which R, R' and R", which may be identical or different, denote a $C_1$-$C_4$ alkyl radical, preferably $CH_3$; a $C_1$-$C_4$ alkoxy radical, preferably methoxy; or OH; A represents a linear or branched, $C_3$-$C_8$ and preferably $C_3$-$C_6$ alkylene radical; m and n are integers dependent on the molecular weight and whose sum is between 1 and 2000.

According to a first possibility, R, R' and R", which may be identical or different, represent a $C_1$-$C_4$ alkyl or hydroxyl radical, A represents a $C_3$ alkylene radical and m and n are such that the weight-average molecular mass of the compound is between 5000 and 500 000 approximately. Compounds of this type are referred to in the CTFA dictionary as "amodimethicones".

According to a second possibility, R, R' and R", which may be identical or different, represent a $C_1$-$C_4$ alkoxy or hydroxyl radical, at least one of the radicals R or R" is an alkoxy radical and A represents a $C_3$ alkylene radical. The hydroxy/alkoxy molar ratio is preferably between 0.2/1 and 0.4/1 and advantageously equal to 0.3/1. Moreover, m and n are such that the weight-average molecular mass of the compound is between 2000 and $10^6$. More particularly, n is between 0 and 999 and m is between 1 and 1000, the sum of n and m being between 1 and 1000.

In this category of compounds, mention may be made, inter alia, of the product Belsil® ADM 652 sold by Wacker.

According to a third possibility, R and R", which are different, represent a $C_1$-$C_4$ alkoxy or hydroxyl radical, at least one of the radicals R or R" is an alkoxy radical, R' represents a methyl radical and A represents a $C_3$ alkylene radical. The hydroxy/alkoxy mole ratio is preferably between 1/0.8 and 1/1.1 and advantageously is equal to 1/0.95. Moreover, m and n are such that the weight-average molecular weight of the compound is between 2000 and 200 000. More particularly, n is between 0 and 999 and m is between 1 and 1000, the sum of n and m being between 1 and 1000.

More particularly, mention may be made of the product Fluid WR® 1300 sold by Wacker.

According to a fourth possibility, R and R" represent a hydroxyl radical, R' represents a methyl radical and A is a $C_4$-$C_8$ and preferably $C_4$ alkylene radical. Moreover, m and n are such that the weight-average molecular mass of the compound is between 2000 and $10^6$. More particularly, n is between 0 and 1999 and m is between 1 and 2000, the sum of n and m being between 1 and 2000.

A product of this type is especially sold under the name DC 28299 by Dow Corning.

It should be noted that the molecular weight of these silicones is determined by gel permeation chromatography (room temperature, polystyrene standard; μ styragem columns; THF eluent; flow rate of 1 mm/m; 200 μl of a solution containing 0.5% by weight of silicone in THF are injected, and detection is performed by refractometry and UV-metry).

A product corresponding to the definition of formula (XIX) is in particular the polymer known in the CTFA dictionary as "trimethylsilyl amodimethicone", corresponding to formula (XX) below:

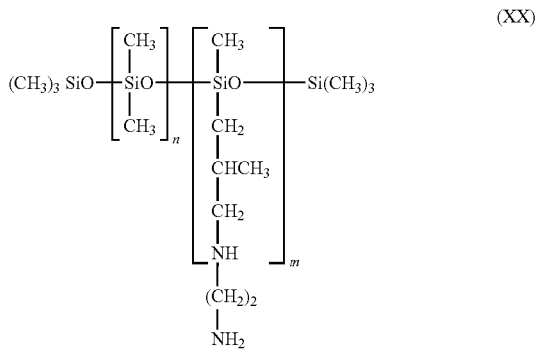

in which n and m have the meanings given above in accordance with formula (XIX).

Such compounds are described, for example, in patent EP 95238; a compound of formula (XX) is sold, for example, under the name Q2-8220 by the company OSI.

(b) the compounds corresponding to formula (XXI) below:

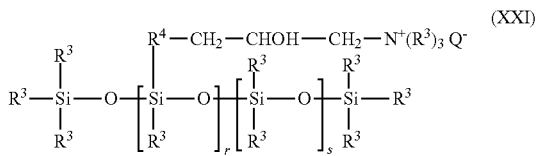

in which:
$R^3$ represents a $C_1$-$C_{18}$ monovalent hydrocarbon-based radical, and in particular a $C_1$-$C_{18}$ alkyl or $C_2$-$C_{18}$ alkenyl radical, for example methyl;
$R^4$ represents a divalent hydrocarbon-based radical, especially a $C_1$-$C_{18}$ alkylene radical or a divalent $C_1$-$C_{18}$, and for example $C_1$-$C_8$, alkylenoxy radical;
$Q^-$ is a halide ion, in particular chloride;
r represents a mean statistical value from 2 to 20 and in particular from 2 to 8;
s represents a mean statistical value from 20 to 200 and in particular from 20 to 50.

Such compounds are described more particularly in patent U.S. Pat. No. 4,185,087.

A compound falling within this class is the product sold by the company Union
Carbide under the name Ucar Silicone ALE 56.

(c) the quaternary ammonium silicones of formula (XXII):

in which:
$R_7$, which may be identical or different, represent a monovalent hydrocarbon-based radical containing from 1 to 18 carbon atoms, and in particular a $C_1$-$C_{18}$ alkyl radical, a $C_2$-$C_{18}$ alkenyl radical or a ring comprising 5 or 6 carbon atoms, for example methyl;
$R_6$ represents a divalent hydrocarbon-based radical, especially a $C_1$-$C_{18}$ alkylene radical or a divalent $C_1$-$C_{18}$, and for example $C_1$-$C_8$, alkylenoxy radical linked to the Si via an SiC bond;
$R_8$, which may be identical or different, represent a hydrogen atom, a monovalent hydrocarbon-based radical containing from 1 to 18 carbon atoms, and in particular a $C_1$-$C_{18}$ alkyl radical, a $C_2$-$C_{18}$ alkenyl radical or a radical —$R_6$—NH-$COR_7$;
$X^-$ is an anion such as a halide ion, especially chloride, or an organic acid salt (acetate, etc.);
r represents a mean statistical value from 2 to 200 and in particular from 5 to 100;

These silicones are described, for example, in patent application EP-A-0 530 974.

(d) the amino silicones of formula (XXIII):

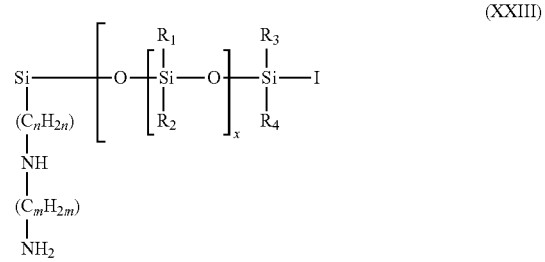

in which:
$R_1$, $R_2$, $R_3$ and $R_4$, which may be identical or different, denote a $C_1$-$C_4$ alkyl radical or a phenyl group,
$R_5$ denotes a $C_1$-$C_4$ alkyl radical or a hydroxyl group,
n is an integer ranging from 1 to 5,
m is an integer ranging from 1 to 5,
and in which x is selected such that the amine number is between 0.01 and 1 meq/g.

The silicone that is particularly preferred is an amodimethicone.

The composition according to the invention preferably comprises from 0.01% to 10% by weight and better still from 0.1% to 5% by weight of silicone(s) relative to the total weight of the composition.

The composition according to the invention may moreover comprise one or more cosmetic additives commonly used in the art, for instance antioxidants, organic ultraviolet screening agents, inorganic ultraviolet screening agents, thickeners, softeners, antifoams, moisturizers, emollients, plasticizers, mineral fillers, clays, mineral colloids, nacres, fragrances, peptizers, preserving agents, fixing or non-fixing polymers

XVI

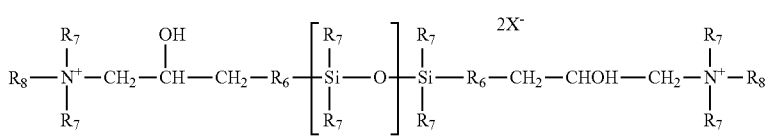

other than the cationic polymers mentioned above, proteins, vitamins and antidandruff agents, and mixtures of these compounds.

A person skilled in the art will take care to select the optional additives and the amounts thereof so that they do not interfere with the properties of the compositions of the present invention.

When they are present, these additives may represent individually an amount ranging from 0.001% to 90% by weight, preferably from 0.001% to 50% by weight and better still from 0.001% to 20% by weight, relative to the total weight of the composition according to the invention.

The composition according to the invention generally comprises water or a mixture of water and one or more organic solvents.

Organic solvents that may be mentioned include lower alcohols ($C_1$-$C_4$), such as ethanol, isopropanol, tert-butanol or n-butanol, polyols such as propylene glycol and glycerol, polyol ethers, $C_5$-$C_{10}$ alkanes, $C_3$-$C_4$ ketones such as acetone, $C_1$-$C_4$ alkyl acetates such as methyl acetate, ethyl acetate and butyl acetate, dimethoxyethane and diethoxyethane, and mixtures thereof.

When the composition according to the invention comprises one or more organic solvents, these solvents may be present in a proportion of from 0.1% to 30% by weight and preferably 0.1% to 10% by weight relative to the total weight of the composition.

The pH of the composition according to the invention, if it is aqueous, generally ranges from 1.5 to 11 and preferably from 2 to 6.5. It may be adjusted to the desired value by means of acidifying or basifying agents usually used in the dyeing of keratin fibres, or alternatively using standard buffer systems.

Among the acidifying agents, examples that may be mentioned include mineral or organic acids, for instance hydrochloric acid, orthophosphoric acid, sulfuric acid and sulfonic acids, and carboxylic acids, for instance acetic acid, tartaric acid, citric acid or lactic acid.

Mention may be made, among the basifying agents, by way of example, of aqueous ammonia, alkaline carbonates, alkanolamines, such as mono-, di- and triethanolamines, and their derivatives, sodium hydroxide, potassium hydroxide and the compounds of formula (XXIV) below:

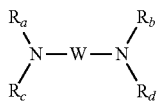

(XXIV)

in which:

W is a propylene residue optionally substituted with a hydroxyl group or a $C_1$-$C_4$ alkyl radical;

$R_a$, $R_b$, $R_c$ and $R_d$, which may be identical or different, represent a hydrogen atom or a $C_1$-$C_4$ alkyl or $C_1$-$C_4$ hydroxyalkyl group.

The composition according to the invention may be in any galenical form normally used for topical application. In particular, the composition according to the invention may be a lotion, a gel, a spray, a mousse or a cream.

The composition according to the invention may be a shampoo, a hair conditioner, a hairsetting product, a dye product, a bleaching product or a permanent-waving product.

Preferably, the composition according to the invention is a hair conditioner.

Another subject of the invention is a cosmetic treatment process that comprises the application to keratin fibres, preferably human keratin fibres such as the hair, and the scalp, of a composition according to the invention as described above, with or without and preferably without subsequent rinsing of the said keratin fibres.

The composition according to the invention that is applied may be massaged on the hair so as to accelerate the penetration, by hand or using any other adequate means, such as a brush or a comb.

The examples that follow are intended to illustrate the invention without, however, being limiting in nature.

The amounts are indicated as weight percentages of active material (AM) relative to the total weight of each composition.

The following compositions were prepared:

EXAMPLE 1

Leave-on Hair Conditioner

| | |
|---|---|
| Hydroxypropyl starch phosphate (Structure ZEA from Akzo Nobel) | 4 |
| Zinc gluconate | 3 |
| Water | qs 100% |

"Starch"/"Zn element" weight ratio = 11.62

EXAMPLE 2

Leave-on Hair Conditioner

| | |
|---|---|
| Hydroxypropyl starch phosphate (Structure ZEA from Akzo Nobel) | 5 |
| Zinc sulfate heptahydrate from Merck | 1.5 |
| Water | qs 100% |

"Starch"/"Zn element" weight ratio = 14.7

EXAMPLE 3

Rinse-off Hair Conditioner

| | % AM |
|---|---|
| Cetyl alcohol (Nafol 1618 EN from Sasol) | 2.5 |
| Myristyl/cetyl/stearyl myristate/palmitate/stearate mixture (Crodamol MS-PA from Croda) | 0.5 |
| Hydroxypropyl starch phosphate (Structure ZEA from Akzo Nobel) | 4 |
| Zinc gluconate (Givobio G Zn from SEPPIC) | 3 |
| Water | qs 100% |

"Starch"/"Zn element" weight ratio = 9.3

EXAMPLE 4

Rinse-off Hair Conditioner

| | % AM |
|---|---|
| Cetyl alcohol (Nafol 1618 EN from Sasol) | 2.5 |
| Myristyl/cetyl/stearyl myristate/palmitate/stearate mixture (Crodamol MS-PA from Croda) | 0.5 |

-continued

|  | % AM |
|---|---|
| Hydroxypropyl starch phosphate (Structure ZEA from Akzo Nobel) | 5 |
| Zinc gluconate (Givobio G Zn from SEPPIC) | 5 |
| Ceteareth-33 (Simulsol CS Ecailles from SEPPIC) | 0.8 |
| Amodimethicone as a nonionic emulsion containing 15% AM (Wacker Belsil PDM LOG 1 from Wacker) | 1 |
| Palm oil (Akofrite RSPO/SG from AAK) | 2 |
| Preserving agents | 0.33 |
| Water | qs 100% |

"Starch"/"Zn element" weight ratio = 6.94

EXAMPLE 5

Rinse-off Hair Conditioner

|  | % AM |
|---|---|
| Cetyl alcohol (Nafol 1618 EN from Sasol) | 2.5 |
| Myristyl/cetyl/stearyl myristate/palmitate/stearate mixture (Crodamol MS-PA from Croda) | 0.5 |
| Hydroxypropyl starch phosphate (Structure ZEA from Akzo Nobel) | 5 |
| Zinc chloride | 4 |
| Ceteareth-33 (Simulsol CS Ecailles from SEPPIC) | 0.8 |
| Amodimethicone as a nonionic emulsion containing 15% AM (Wacker Belsil PDM LOG 1 from Wacker) | 0.9 |
| Crosslinked ethyltrimethylammonium methacrylate chloride homopolymer (Salcare SC 95 from Ciba) | 0.15 |
| Preserving agents | 0.33 |
| Water | qs 100% |

"Starch"/"Zn element" weight ratio = 2.6

EXAMPLE 6

Rinse-out Hair Conditioner

|  | % AM |
|---|---|
| Cetyl alcohol (Nafol 1618 EN from Sasol) | 2.5 |
| Myristyl/cetyl/stearyl myristate/palmitate/stearate mixture (Crodamol MS-PA from Croda) | 0.5 |
| Hydroxypropyl starch phosphate (Structure ZEA from Akzo Nobel) | 5 |
| Zinc gluconate (Givobio G Zn from SEPPIC) | 5 |
| Ceteareth-33 (Simulsol CS Ecailles from SEPPIC) | 0.8 |
| Amodimethicone as a nonionic emulsion containing 15% AM (Wacker Belsil PDM LOG 1 from Wacker) | 1 |
| Palm oil (Akofrite RSPO/SG from AAK) | 2 |
| Preserving agents | 0.33 |
| Water | qs 100% |

"Starch"/"Zn element" weight ratio = 6.94

All the compositions have a pH of about 5.

The formulations of the six examples are stable over time. The compositions are applied to wet hair and the hair is then dried. The dry hair has a smooth feel, disentangles easily and appears denser.

A composition according to the invention (composition 6) was compared with a comparative composition (composition 6B) not comprising any zinc salt. When applied to wet hair, composition 6 gives the hair, after drying, better ease of the disentangling, more suppleness and more smoothness on dry hair than composition 6B.

Results equivalent to those obtained with composition 6 are obtained by replacing the 5% of Structure ZEA (Akzo Nobel) with 2.5% of sodium carboxymethyl starch (Primojel from DMV International).

The invention claimed is:

1. A cosmetic composition comprising:
   at least one non-nitrogenous zinc salt, and
   at least one starch,
   wherein the weight ratio of the amount of the at least one starch to the amount of zinc element ranges from about 1 to about 25.

2. The composition according to claim 1, wherein the at least one non-nitrogenous zinc salt is chosen from mineral salts.

3. The composition according to claim 1, wherein the at least one non-nitrogenous zinc salt is chosen from zinc sulfate and zinc chloride.

4. The composition according to claim 1, wherein the at least one non-nitrogenous zinc salt is chosen from organic salts.

5. The composition according to claim 1, wherein the at least one non-nitrogenous zinc salt is chosen from zinc lactate, zinc gluconate, zinc phenolsulfonate, zinc citrate, zinc salicylate, and derivatives thereof corresponding to the formula:

$$\left[ (R_1)_p \underset{}{\underset{}{\bigcirc}} \begin{matrix} COO^- \\ OH \end{matrix} \right]_n Zn^{2+}$$

wherein:
   n is 2;
   p is chosen from 0, 1, 2 and 3; and
   $R_1$ is chosen from linear and branched $C_1$-$C_{18}$ alkyl groups; linear and branched $C_1$-$C_{18}$ hydroxyalkyl groups; halogen atoms; $C_2$-$C_{18}$ acyl groups; groups $COR_2$, $OCOR_2$, and $CONHR_2$, wherein $R_2$ is chosen from hydrogen atoms and linear and branched $C_1$-$C_{18}$ alkyl groups.

6. The composition according to claim 1, wherein the at least one non-nitrogenous zinc salt is chosen from zinc lactate and zinc gluconate.

7. The composition according to claim 1, wherein the at least one non-nitrogenous zinc salt is zinc gluconate.

8. The composition according to claim 1, wherein the concentration of the at least one non-nitrogenous zinc salt ranges from about 0.1% to about 10% by weight, relative to the total weight of the composition.

9. The composition according to claim 1, wherein the concentration of the at least one non-nitrogenous zinc salt ranges from about 0.5% to about 6.5% by weight, relative to the total weight of the composition.

10. The composition according to claim 1, wherein the concentration of the at least one non-nitrogenous zinc salt is less than about 2% by weight, relative to the total weight of the composition.

11. The composition according to claim 1, wherein the concentration of the at least one non-nitrogenous zinc salt ranges from about 0.005% to about 1.5% by weight, relative to the total weight of the composition.

12. The composition according to claim 1, wherein the at least one starch originates from a plant source chosen from corn, pea, potato, sweet potato, banana, barley, wheat, rice, oat, sago, tapioca, and sorghum.

13. The composition according to claim 1, wherein the at least one starch is chosen from optionally hydroxypropylated starch phosphates, starches modified with 2-chloroethylaminopropionic acid, and carboxymethyl starches.

14. The composition according to claim 1, wherein the at least one starch is present in an amount ranging from about 0.01% to about 15% by weight, relative to the total weight of the composition.

15. The composition according to claim 1, wherein the at least one starch is present in an amount ranging from about 0.2% to about 8% by weight, relative to the total weight of the composition.

16. The composition according to claim 1, wherein the weight ratio of the amount of the at least one starch to the amount of zinc element ranges from about 1 to about 20.

17. The composition according to claim 1, further comprising at least one additive chosen from fatty alcohols, cationic polymers, cationic surfactants, and silicones.

18. The composition according to claim 1, wherein the composition is in the form of a leave-on hair care product.

19. A cosmetic process for treating keratin fibers comprising:
    applying to the keratin fibers and/or scalp a composition comprising at least one non-nitrogenous zinc salt and at least one starch, wherein the weight ratio of the amount of the at least one starch to the amount of zinc element ranges from about 1 about 25, and optionally rinsing the composition from the keratin fibers and/or scalp.

20. The process according to claim 19, wherein the process for treating keratin fibers is chosen from processes that condition the keratin fibers and/or protect artificial color of the keratin fibers from fading.

\* \* \* \* \*